(12) United States Patent
Chiu

(10) Patent No.: US 7,811,514 B2
(45) Date of Patent: Oct. 12, 2010

(54) STOPPABLE TEST DEVICE

(76) Inventor: John Chiu, 18422 Roslin Ave., Suite 1, Torrance, CA (US) 90540

( * ) Notice: Subject to any disclaimer, the term of this patent is extended or adjusted under 35 U.S.C. 154(b) by 748 days.

(21) Appl. No.: 11/762,780

(22) Filed: Jun. 14, 2007

(65) Prior Publication Data

US 2008/0311003 A1     Dec. 18, 2008

(51) Int. Cl.
*G01N 21/00*     (2006.01)

(52) U.S. Cl. .......................................... 422/57

(58) Field of Classification Search .................... 422/57
See application file for complete search history.

*Primary Examiner*—Walter D Griffin
*Assistant Examiner*—Bobby Ramdhanie

(57) ABSTRACT

A lateral flow chromatography test device is disclosed that includes a stopping mechanism which enables a user of the test device to stop reactions of a test by pushing the stopping mechanism downward to remove materials flowing along a test strip in the test device at a time instructed by the manufacturer or decided by the user. This stopping mechanism is adapted to freeze the test result at the stopping time so as to keep the test result as a permanent record. The invention enables qualitative tests to become quantitative or semi-quantitative tests.

14 Claims, 5 Drawing Sheets

STOPPABLE TEST DEVICE

BACKGROUND OF THE INVENTION

1. Field of Invention

The invention relates to immunoassay test devices and more particularly to a test device having a stopping mechanism adapted to freeze a test result at a stopping time so as to keep the test result as a permanent record and enable the qualitative tests to become quantitative or semi-quantitative tests.

2. Description of Related Art

Interruption of chemical, biochemical, or immunological reaction requires the removal and/or separation of reactants, intermediates, products, or reaction mediums from the reaction mixture, or changes of the temperature, reactants, or physical parameter of the reaction mixture. The interruption procedures usually demand tedious manipulations and extra time. Therefore, most rapid tests produce qualitative results only rather than produce quantitative or semi-quantitative test results. Undoubtedly, a simple, easy, rapid, and inexpensive method to terminate the reaction in situ will be useful to all users.

There have been numerous suggestions in prior patents for lateral flow chromatographic immunoassay methods and devices. For example, U.S. Pat. No. 4,956,302 to Gordon and Pugh; WO 90/06511 to H. Buck, et al; U.S. Pat. No. 6,764,825 to T. Wang; U.S. Pat. No. 5,008,080 to W. Brown, et al; and U.S. Pat. No. 6,183,972 to Kuo and Meritt. This technique has been commercialized for the productions of easy-to-use rapid diagnostic tests, such as Clearblue One-Step Pregnancy Test in 1988 (EP 291194; EP 560411). The One-Step Immunodiagnostic Test can show qualitative result rapidly. However, it cannot provide quantitative or semi-quantitative result because, among other reasons, there is no mechanism to terminate the reaction at a fixed time. Hence the intensity of the result signal varies continuously with time.

Qualitative test provides yes or no (i.e., positive or negative) data to the presence of the antigen (the analyte to be detected) in the sample solution, whereas quantitative or semi-quantitative test provides the data of the amount or the level of the amount of the antigen in the sample, which are more informative and important to the test users. For example, a positive drug of abuse test result has no legal meaning unless the amount of drug exceeds the legal limit. Also, there is always a background level of Luteinizing Hormone (LH) in the woman's body fluids. When the LH level has surged to a certain level the ovulation will then occur in 1-2 days (K. Elkind-Hirsch, et al, Obstetric and Gynecology, 67 (3):4450, 1986). Therefore, qualitative test cannot provide any useful information for LH diagnosis, because both the background and the surged levels of body fluid samples will give the same positive results. Detection of the Prostate Specific Antigen (PSA) levels at 4 ng/ml or less has no diagnostic significance, even though a positive result is shown in a qualitative test. The PSA levels higher than 4 ng/ml have different etiological significance (H. Rittenhouse, et al, Critical Rev. in Clin. Lab. Sci., 35(4):275, 1998; W. Catalona, et al, J. Am. Med. Asso., 274(15):1214, 1995). The C-Reactive Protein (CRP) levels reflect the kind and severity of different symptoms (L. Powell, Am. J. Med. Technol., 87:138, 1979; N. Rifai and P. Ridkeer, Clin. Chem., 47:28, 2001; P. Ridker, et al, Circulation, 97:425, 1998). Qualitative tests cannot differentiate the levels of the antigen amounts and provide early warning signals and information. The levels of Human Chorionic Gonadotropin (HCG) can provide useful information for the detection and the monitoring of pregnancy, ectopic pregnancy, threatened abortion, or selected malignancies of trophoblastic and non-trophoblastic origin (R. Frances and M. Batzer, Fertil. Steril., 34:1, 1980; M. Dhont, et al, Lancet, i:559, 1978; N. Kadar and R. Romero, Lancet, i:1205, 1981; P. Jouppila, et al, Br. J. Obstet. Gynecol., 86:343, 1979; H. Bates, Lab. Manag., 18:25, 1980; M. Dawood, et al, Obstet. Gynecol., 50:172, 1977; P. Papepetrou, et al, Cancer, 45:2583, 1980). Clearly, while keeping the advantages of low cost, quickness, simplicity, and versatility of the well known One-Step Immunodiagnostic Test, endowing it with semi-quantitative or quantitative detection capacity will be extremely useful and popular in the field of medical diagnostics and diagnostic testing in general.

Thus, it is desirable to provide a novel stoppable test device having a stopping mechanism for the One-Step Test, as well as for other tests and reactions, so that quantitative or semi-quantitative data can be obtained rapidly and easily with a simple test device.

SUMMARY OF THE INVENTION

It is therefore one object of the invention to provide a lateral flow chromatography test device having a stopping mechanism adapted to have its legs to remove materials flowing along a test strip, thereby permanently stopping ongoing reactions on the test strip. By utilizing this test device, a test result can be kept as a permanent record and thus the invention enables qualitative tests to become quantitative or semi-quantitative tests.

The above and other objects, features and advantages of the invention will become apparent from the following detailed description taken with the accompanying drawings.

DETAILED DESCRIPTION OF THE INVENTION

Principles of the invention is described in detail below. The establishment of lateral flow test is based on the continuous flow of liquid sample through all reaction domains. Therefore, isolation of one reaction domain will stop all reactions. The invention is directed to a test device having a stopping mechanism adapted to stop the ongoing reactions by simply pushing the stopping mechanism downward.

A typical lateral flow test is a plastic housing containing a test strip. The invention can use the test strip of the typical One-Step Test directly without any modification, which is a plastic strip laminated with porous materials for liquid to flow through laterally. The flow through section of the test strip usually is divided into four domains, which can be made of only one kind of material or up to four different kinds of materials. The first domain is for sample addition. It functions to remove viscous and particulate materials in the sample and also to condition the sample solution for the reactions in the following domains. The second domain is a mobile-phase with "color conjugate". The "color conjugate" is made from conjugation between a "visible color marker" and a "detection antibody" which can bind a specific antigen in the sample (the analyte to be detected) and forms "antigen-color conjugate complex." The third domain is a solid-phase with immobilized "capture antibody". The "capture antibody" can bind the antigen of the "antigen-color conjugate complex" and forms "capture antibody-antigen-color conjugate complex" sandwich. The fourth domain is for solution absorption. It draws sample solution towards it continuously. During the testing, sample added to the first domain flows to the second domain. If the antigen is present in the sample, it will bind the "color conjugate" to form "antigen-color conjugate complex." This complex then migrates to the third domain to bind the "capture antibody" and forms the "capture antibody-antigen-color conjugate complex" sandwich. Since the "capture antibody" is immobilized in the third domain, the sandwich shows as a "visible color signal" on the site of the "capture antibody." If there is no antigen in the sample, no sandwich can be formed and hence no "visible color signal" can be seen in the third domain. Eventually, almost all of the sample solution will flow into the fourth domain and be absorbed by the absorbent pad.

Figure 1:
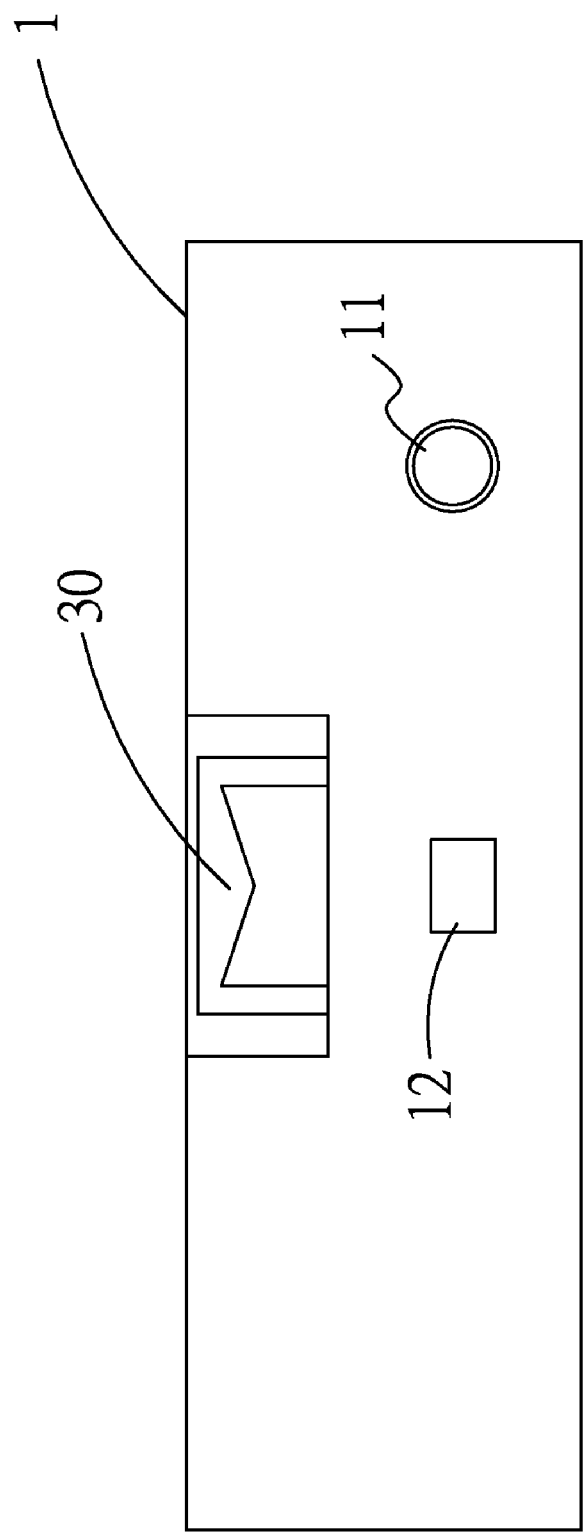
FIG. 1 is a front view of a preferred embodiment of stoppable test device according to the invention.
Figure 2:
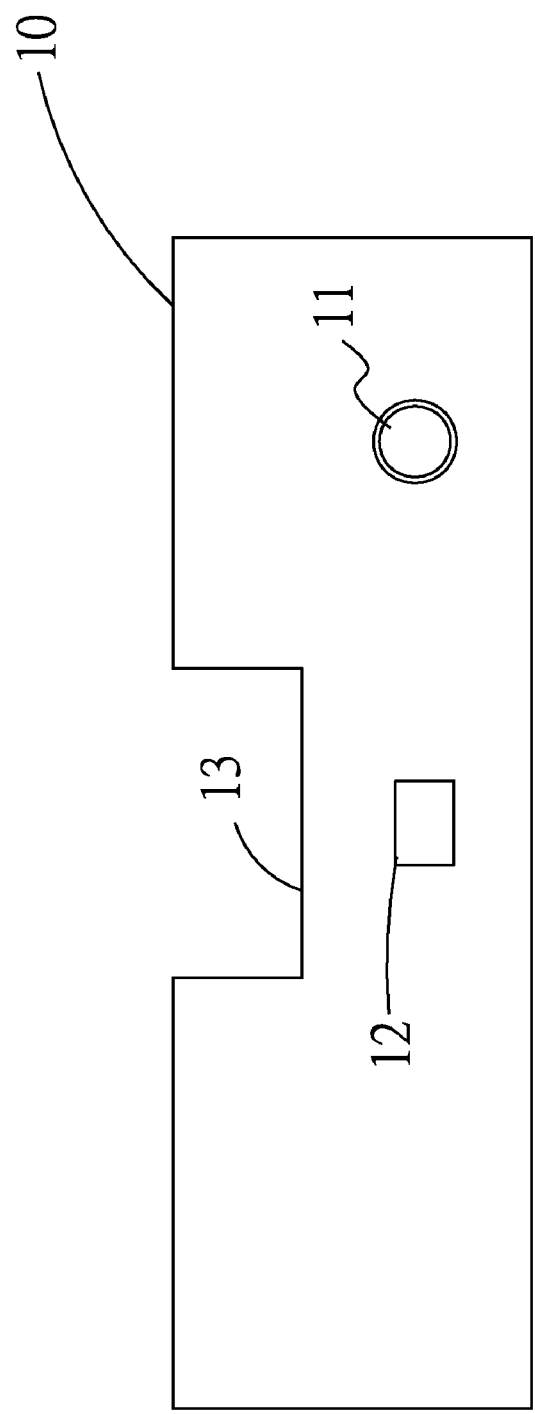
FIG. 2 is a front view of the cover of the test device.
Figure 3:
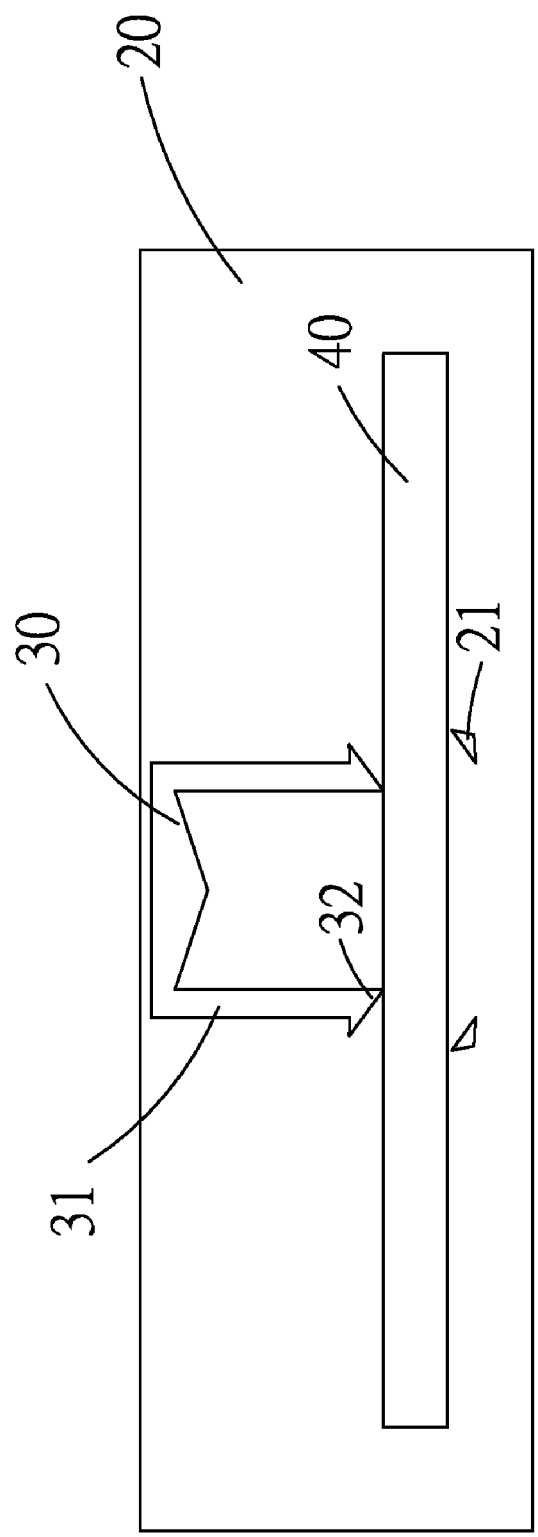
FIG. 3 is a front view of the base of the test device.

Referring to FIGS. 1 to 3, a stoppable test device 1 in accordance with a preferred embodiment of the invention is shown. The test device 1 is substantially rectangular and comprises a plastic cover 10 and a plastic base 20 having a bottom edge flexibly formed with a bottom edge of the cover 10 so that in one operation the test device 1 can be opened by disengaging a top edge of the cover 10 with that of the base 20 and in the other operation the test device 1 can be closed by lockingly engaging the top edge of the cover 10 with that of the base 20 by snapping. The test device 1 further comprises a plastic M-shaped stopping mechanism 30. Each component is discussed in detail below.

The base 20 comprises two spaced lock members 21 proximate a bottom edge. The stopping mechanism 30 is movably positioned on the base 20 by guide members (e.g., grooves or the like not shown) and is disposed above the lock members 21. The stopping mechanism 30 has an interconnecting portion being proximate a top edge of the base 20 in an inoperative position. The stopping mechanism 30 comprises two legs 31 having a latched end 32 having teeth (or parallel ribs in other embodiments) formed thereon. The latched end 32 is shaped to be adapted to lockingly engage with the lock member 21 as detailed later.

A lateral test strip 40 is secured onto the base 20 and is disposed between the lock members 21 and the stopping mechanism 30 in an inoperative position.

The cover 10 comprises a rectangular top recess 13 for exposing a portion of the stopping mechanism 30 in an inoperative position, a rectangular window 12 located below the recess 13 and right above the immobilized "capture antibody" on the third domain of the test strip 40 underneath, and a circular well 11 to the right of the window 12.

Figure 4:
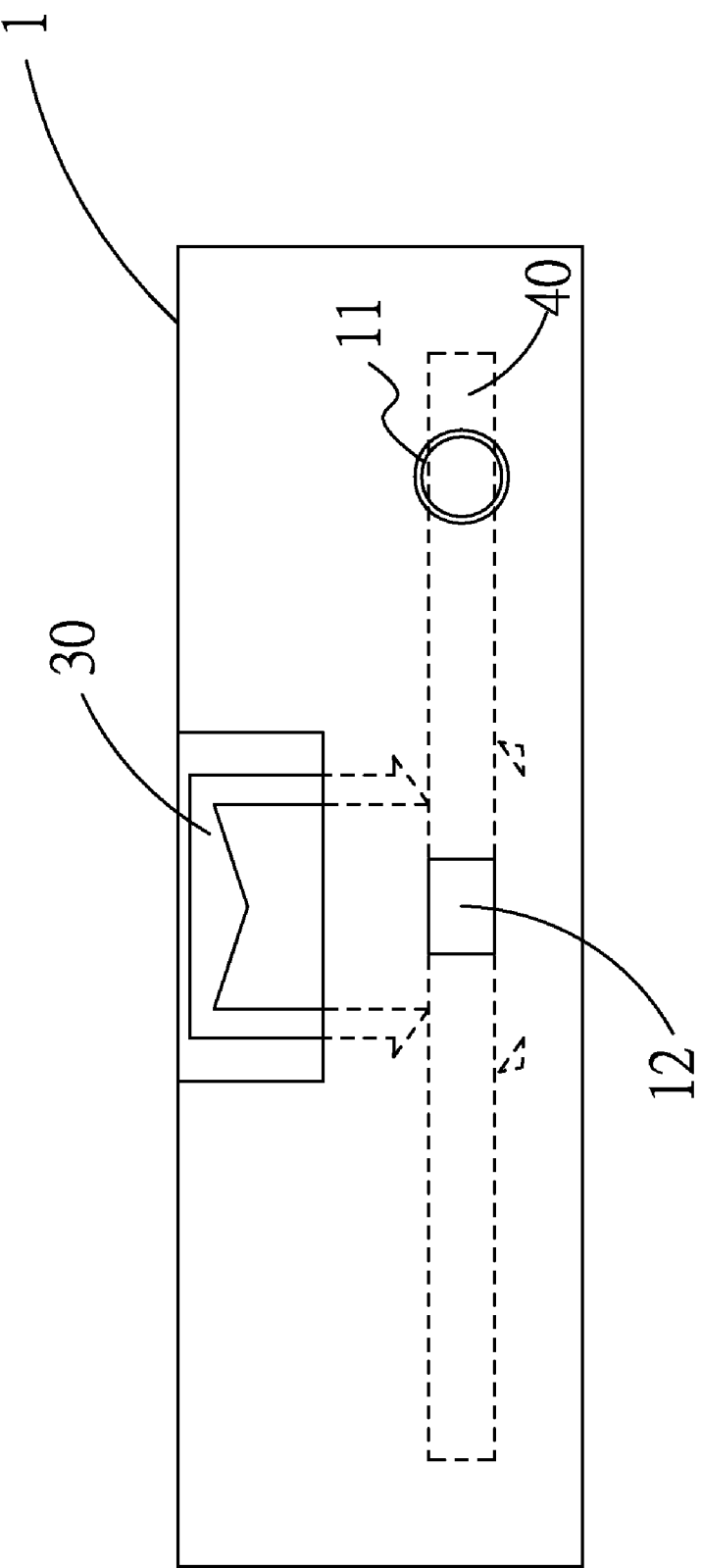
FIG. 4 is a view similar to FIG. 1 where the stopping mechanism has not been pushed down.
Figure 5:
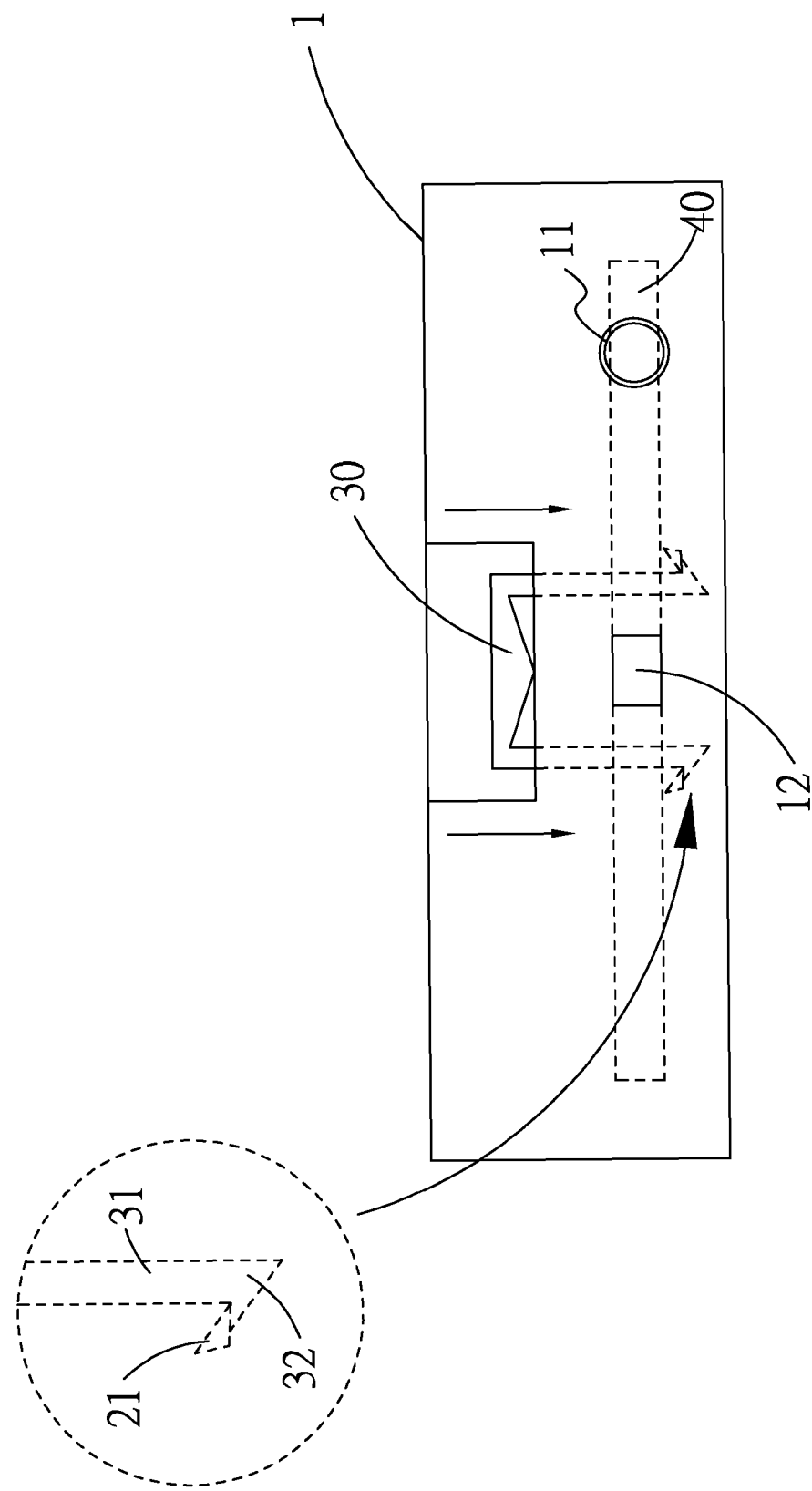
FIG. 5 is a view similar to FIG. 4 where the stopping mechanism has been pushed down to its locked position for freezing a test result.

Referring to FIGS. 4 and 5 in conjunction with FIGS. 1 to 3, an operation of the invention will be described in detail below. A user may first add a sample solution through the well 11 to the first domain of the test strip 40 thereunder. The sample solution then moves laterally in a direction from the well 11 at one end of the test strip 40 to the other end of the test strip 40. After passing a predetermined time (e.g., 5-minute), the user may push the interconnecting portion of the stopping mechanism 30 downward to cause the teeth at the latched ends 32 to scrape off or push off materials such as nitrocellulose on the third domain of the test strip 40. Hence, the ongoing reactions on the test strip 40 are stopped. The pushing will be stopped when the latched ends 32 pass the test strip 40 to lockingly engage with the lock members 21 by flexibly deforming. As an end, the test result is frozen and the user can observe the test result through the window 12. The test result can be kept as a permanent record and thus the invention enables the qualitative tests to become quantitative or semi-quantitative tests.

While the above embodiment discussing teeth being formed at both latched ends 32 is only a preferred embodiment of the invention, it is apparent that the invention can be embodied by forming teeth at only one latched end 32. Moreover, the stopping mechanism 30 may have two legs 31 at either side in other preferred embodiments of the invention.

EXAMPLE 1

This example provides a test and a control to demonstrate that the reactions of the One-Step lateral flow chromatography immunoassay can be stopped with the invention and the test results can be kept as permanent records.

The pregnancy test strip at 4 mm×60 mm, for the detection of HCG, was prepared (Vanguard Biomedical Corporation, USA). The sample pad filter paper (Schleicher & Schuell, Germany) at 4 mm×12 mm was treated with 50 mM Tris buffer saline with 0.1% Tween 20, pH 8.3 and air dried at room temperature overnight, then dried at 45° C. with blowing air in an oven for one hour. The conjugate pad glass fiber at 4 mm×6 mm was treated with 20 μl of conjugate, OD at 530 nm=1.5, made from 40 nm colloidal gold and a monoclonal anti-beta-HCG antibody (Medix Biochemica, Finland) and dried in a lyophilizer at 25° C. for 5 hours. The nitrocellulose membrane at 4 mm×25 mm (Sartorius, Germany) was spotted with 10 ng of another monoclonal anti-beta-HCG antibody (Medix Biochemica, Finland) in 10 mM Tris buffered saline, pH 8.3 at the center region of the nitrocellulose and air dried at room temperature overnight. The absorption domain is an absorbent paper at 4 mm×19 mm (Schleicher & Schuell, Germany). To assemble the test strip, a plastic strip (G & L, USA) at 4 mm×60 mm with double adhesive was attached with the membrane at about the center location. The absorption paper was attached to one end of the plastic strip, with a slight overlap with the membrane. The conjugate pad was attached to the other end of the plastic strip, with slight overlap with the membrane, followed by another attachment of the sample pad, with slight overlap with the conjugate pad. Finally, one test strip was assembles in a regular One-Step test cassette (Vanguard Biomedical Corporation, USA) as the control; and another identical test strip was assembled in the stoppable test device of the invention (FIG. 4) as the test.

Both test devices were added with 0.2 ml of pregnant woman's urine (two weeks after her missed period). Both showed strong "visible color signals," the positive results, in less than 5 minutes. At the 5-minute time, both the control and test devices showed result signals with identical intensity. The reaction in the test device of the invention was stopped by pushing the M-shaped stopping mechanism downward. The result signals of both the control and test devices were re-examined 20 minutes later. By then, the control device showed a stronger signal while the signal intensity of the test device of the invention remained the same. After another 20 minutes, the signal of the control device intensified further while the signal in the test device still remained the same as that at the 5-minute time. This test device with the stopping mechanism was then opened for examination. This examination revealed that the stopping mechanism had physically removed the portion of nitrocellulose on the test strip located in the passage of the teeth movement.

EXAMPLE 2

This example demonstrates the invention can improve the qualitative test device for quantitative testing.

Test strips identical to those in Example 1 were prepared. Test devices of the invention were used to house the test strips. Each test device was added with 0.2 ml of PBS-BSA buffer containing 50, 200, or 1,000 mIU/ml of HCG (First IRP from the WHO) respectively. Three sets of this testing were performed. All tests were stopped at the 5-minute time. The results showed (1) signal intensities did not change after the 5-minute time, (2) the signal intensity had dosage response, and (3) all three tests using identical HCG concentration showed same signal intensity. Clearly, this experiment demonstrates that the invention can produce consistent and reproducible results, and the amount of the analyte in a sample can be estimated or figured out by comparing its result signal with those of known standards. Therefore, the invention can be used to do the quantitative or semi-quantitative testing.

EXAMPLE 3

This example shows the test results obtained from the use of the invention can be kept as permanent records as well as used for day-to-day comparisons.

Test strips similar to those in Example 1 were prepared, excepting that the anti-HCG antibodies were replaced by anti-LH antibodies (Medix Biochemica, Finland). The test strips were assembled in the stoppable test device of the invention. Six test devices with a user instruction sheet were given to a 28 year old woman. This woman started her first testing on the 12th day after her last period, and continued the testing for a total of six days. Each day at around 10 AM she used the invention to test on her fresh urine sample. At the 5-minute time she stopped the reaction by pushing down the M-shaped stopping mechanism then saved the test device for the records and for day-to-day comparisons. The test results of the first two days showed very faint result signals, indicating the background level of LH. The third day showed a slightly stronger signal, indicating LH surge was coming. The fourth day showed a very strong result signal, showing the surge level of LH is present in the urine and ovulation will occur in 1-2 days. The fifth day showed a result signal with median intensity. The sixth day showed signal intensity near to the background level. This set of six test devices were kept and re-examined ten days later, the signal appearances remained the same and the profile of signal intensity for the ovulation prediction also remained intact.

ADVANTAGES OF THE INVENTION

One-Step lateral flow chromatography immunoassay is simple, easy, rapid, and inexpensive. However, this test can provide qualitative data only because there is no mechanism to stop the testing so that test result signal will continue to change with time, resulting false positive or false negative signals. Such signal changes are derived from continuous reaction, evaporation, back flowing, and chemical and/or physical deteriorations of components. Although for qualitative detection purpose the users can call the test results at the predetermined time, it is inconvenient for the users, particularly for the busy professionals such as nurses and doctors. Besides, this kind of test results cannot be kept as permanent records, and cannot be used for day-to-day comparisons, such as for the ovulation prediction test. The invention provides a stopping mechanism which can terminate the reaction at a pre-determined time or at a time chosen by the end users to freeze the test result. With this stoppable test device, users can stop the reaction, walk away and perform other tasks, come back and check the permanent record later at any time. With this stoppable test device, the door for simple, easy, rapid, and inexpensive quantitative and semi-quantitative diagnostic testing is also opened.

For quantitative testing, the stopped result signals can be compared with result signals obtained from standard solutions, or with a standard color chart. For semi-quantitative testing, the stopped result signals can be compared with result signals obtained from standard solutions, or with a standard color chart which indicates the intensity of the signal. Alternatively, the number of the signal lines can represent certain levels of the analyte concentrations in a semi-quantitative test.

The M-shaped stopping mechanism is inexpensive and effective, adding only a fraction of total production cost and providing a greater than 99% efficacy. It does not reduce or interfere with the stability, sensitivity, specificity, reliability, function, and performance of original testing. It is made of plastic and has no metal or knife components. It is safe and easy to assemble and to dispose of. When in use, a simple push down movement will lock it into an irreversible position. No extra additions of solution or manipulations are required. No complicated calculations are required for result interpretation. Moreover, the width and the shape of the stopping mechanism can be adjusted or modified to suit particular needs of an individual test. The number of the leg on the M-shaped stopping mechanism can also be increased to meet requirements. Furthermore, if the test device is used with a reader, the stopping movement can be pre-programmed and executed by the reader.

While the invention herein disclosed has been described by means of specific embodiments, numerous modifications and variations could be made thereto by those skilled in the art without departing from the scope and spirit of the invention set forth in the claims.

What is claimed is:

1. A lateral flow, chromatography test device comprising:
   a base including two spaced lock members proximate a bottom edge;
   a lateral test strip secured onto the base and disposed between the lock members and the stopping mechanism; and
   a cover having a bottom edge flexibly formed with the bottom edge of the base and including a top recess for exposing a portion of a stopping mechanism in an inoperative position, a window located below the recess and above a portion of the test strip, and a well spaced from and laterally aligned with the window,
   whereby adding a sample solution through the well to the test strip, after passing a predetermined period of time; the stopping mechanism movably positioned on the base and including at least one leg at each of two sides, each leg having a latched end having a scraping member, and a member interconnecting both sides; wherein the scraping members of the stopping mechanism physically remove a portion of nitrocellulose on the test strip located in the passage of the scraping member movement; and whereby pushing the interconnecting member downward will cause the scraping members to further remove materials on the test strip below the latched ends until lockingly engage the latched ends with the lock members, thereby permanently stopping ongoing reactions on the test strip.

2. The lateral flow chromatography test device of claim 1, wherein the scraping members are teeth.

3. The lateral flow chromatography test device of claim 1, wherein the number of the leg at either side is one.

4. The lateral flow chromatography test device of claim 1, wherein the number of the leg at either side is two or more.

5. The lateral flow chromatography test device of claim 1, wherein pushing the interconnecting member downward is performed manually or mechanically.

6. The lateral flow chromatography test device of claim 1, wherein permanently stopping ongoing reactions on the test strip stops signal changes caused by the ongoing reactions.

7. The lateral flow chromatography test device of claim 1, wherein permanently stopping ongoing reactions on the test strip is for a quantitative or a semi-quantitative detection of analytes in the sample solution.

8. A lateral flow chromatography test device comprising:
   a base including two spaced lock members proximate a bottom edge;
   a lateral test strip secured onto the base and disposed between the lock members and the stopping mechanism; and
   a cover having a bottom edge flexibly formed with the bottom edge of the base and including a top recess for exposing a portion of a stopping mechanism in an inoperative position, a window located below the recess and above a portion of the test strip, and a well spaced from and laterally aligned with the window,
   whereby adding a sample solution through the well to the test strip, after passing a predetermined period of time; the stopping mechanism movably positioned on the base and including at least one leg at each of two sides, each leg having a latched end having a scraping member, and a member interconnecting both sides; wherein the scraping members of the stopping mechanism physically remove a portion of nitrocellulose on the test strip located in the passage of the scraping member movement; and whereby pushing the interconnecting member downward will cause the at least one scraping member to further remove materials on the test strip below the latched ends until lockingly engage the latched ends with the lock members, thereby permanently stopping ongoing reactions on the test strip.

9. The lateral flow chromatography test device of claim 8, wherein each of the at least one scraping member includes teeth.

10. The lateral flow chromatography test device of claim 8, wherein the number of the leg at either side is one.

11. The lateral flow chromatography test device of claim 8, wherein the number of the leg at either side is two or more.

12. The lateral flow chromatography test device of claim 8, wherein the pushing the interconnecting member downward is performed manually or mechanically.

13. The lateral flow chromatography test device of claim 8, wherein permanently stopping ongoing reactions on the test strip stops signal changes caused by the ongoing reactions.

14. The lateral flow chromatography test device of claim 8, wherein permanently stopping ongoing reactions on the test strip is for a quantitative or a semi-quantitative detection of analytes in the sample solution.

* * * * *